US009378662B2

(12) United States Patent  
Carroll et al.

(10) Patent No.: US 9,378,662 B2  
(45) Date of Patent: Jun. 28, 2016

(54) SIMPLIFIED SPINE TESTING DEVICE

(75) Inventors: Norman L. Carroll, Butler, PA (US); Edward C. Cartwright, New Castle, PA (US); Robert J. Gephardt, Indiana Township, PA (US); Christopher L. Dixon, Indiana Township, PA (US); Vijay K. Goel, Holland, OH (US); Elizabeth A. Friis, Lawrence, KS (US)

(73) Assignees: ATS HOLDINGS LLC, Butler, PA (US); The University of Kansas, Lawrence, KS (US); The University of Toledo, Toledo, OH (US)

( * ) Notice: Subject to any disclaimer, the term of this patent is extended or adjusted under 35 U.S.C. 154(b) by 347 days.

(21) Appl. No.: 14/236,121

(22) PCT Filed: Aug. 6, 2012

(86) PCT No.: PCT/US2012/049682  
§ 371 (c)(1),  
(2), (4) Date: May 5, 2014

(87) PCT Pub. No.: WO2013/020125  
PCT Pub. Date: Feb. 7, 2013

(65) Prior Publication Data  
US 2014/0245844 A1 Sep. 4, 2014

Related U.S. Application Data

(60) Provisional application No. 61/515,105, filed on Aug. 4, 2011.

(51) Int. Cl.  
*A61F 2/46* (2006.01)  
*G09B 23/30* (2006.01)  
(Continued)

(52) U.S. Cl.  
CPC *G09B 23/30* (2013.01); *G01N 3/08* (2013.01); *G01N 3/20* (2013.01); *A61F 2/468* (2013.01)

(58) Field of Classification Search  
CPC .................. A61F 2/468; A61B 5/4566; G01N 2203/0246; G09N 23/32  
See application file for complete search history.

(56) References Cited

U.S. PATENT DOCUMENTS 5,337,758 A * 8/1994 Moore ................. A61B 5/1116  
                                                                          473/209  
7,040,177 B2 * 5/2006 Zubok ..................... A61F 2/468  
                                                                          73/804

(Continued)

OTHER PUBLICATIONS

The International Bureau of WIPO, International Preliminary Report on Patentability issued in PCT/US2012/049682, Feb. 4, 2014, 5 pages.

(Continued)

*Primary Examiner* — David A Rogers  
(74) *Attorney, Agent, or Firm* — Leech Tishman Fuscaldo & Lampl; Kenneth D'Alessandro, Esq.

(57) ABSTRACT

A sample testing device includes a motor, a gear reducer, and an output shaft coupled for rotation by the motor via the gear reducer. The sample testing device further includes a first device adapted to enable the output shaft to move linearly in a first direction substantially parallel with an axis of the output shaft and a second device coupled to the first device for enabling the output shaft to move linearly in a second direction substantially perpendicular to the first direction. The sample testing can further include a third device coupled to the first and second devices for enabling the output shaft to translate linearly in a third direction substantially perpendicular to the first and second directions.

20 Claims, 19 Drawing Sheets

(51) Int. Cl.
*G01N 3/08* (2006.01)
*G01N 3/20* (2006.01)

(56) References Cited

U.S. PATENT DOCUMENTS

| | | | | | |
|---|---|---|---|---|---|
| 7,823,460 | B2* | 11/2010 | White | ................... | A61F 2/468 73/804 |
| 7,895,899 | B2* | 3/2011 | Kelly | ................... | A61B 5/1126 73/760 |
| 2006/0272424 | A1* | 12/2006 | Zubok | ................... | A61F 2/468 73/804 |
| 2007/0260319 | A1* | 11/2007 | Reah | ................... | A61F 2/468 623/17.16 |
| 2008/0257057 | A1* | 10/2008 | Habeger | ................... | A61F 2/468 73/808 |

OTHER PUBLICATIONS

United States Patent and Trademark Office, International Search Report issued in PCT/US2012/049682, Nov. 6, 2012, 2 pages.

* cited by examiner

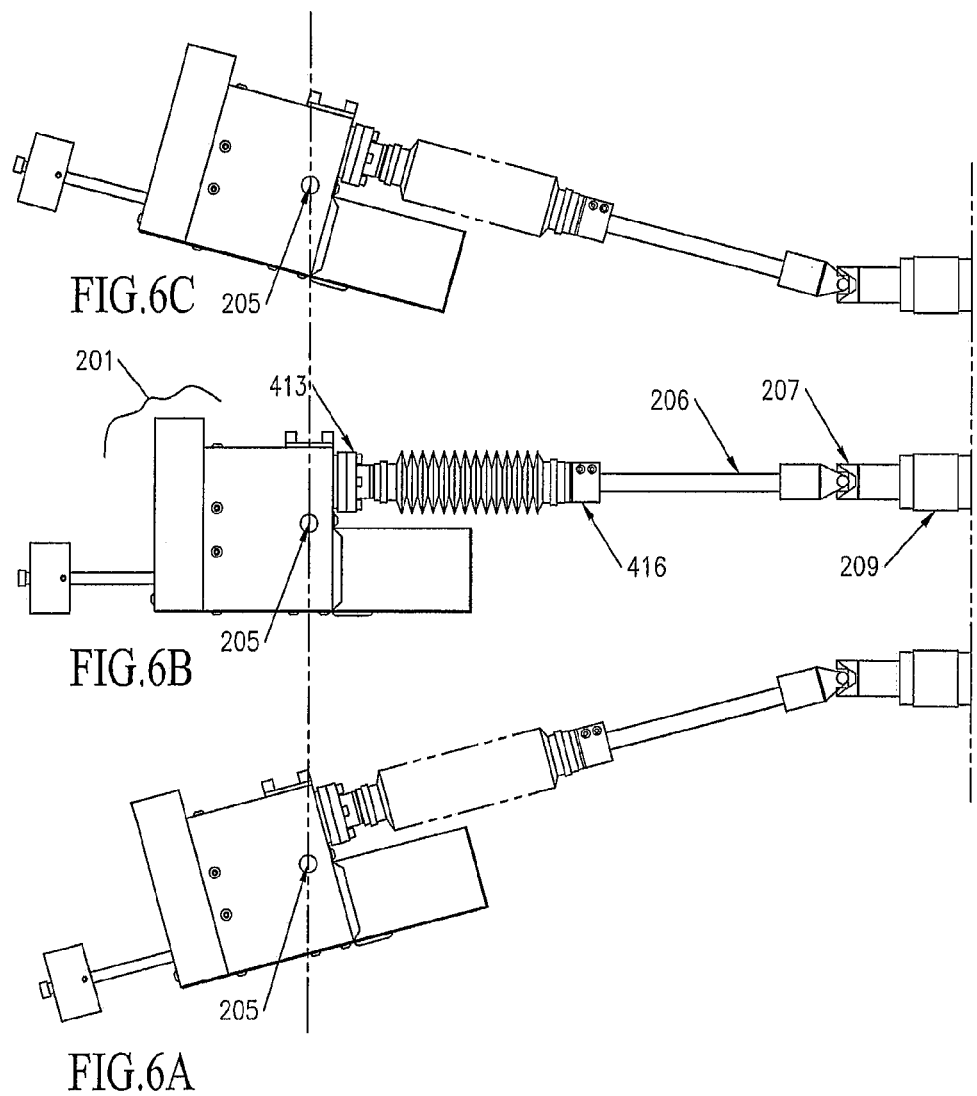

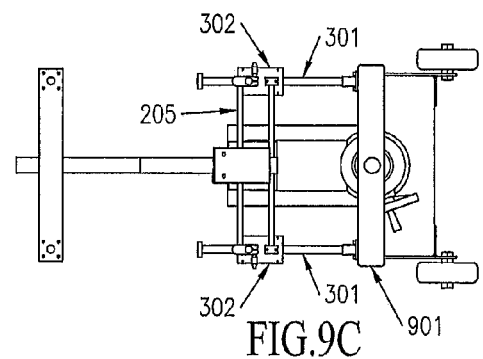
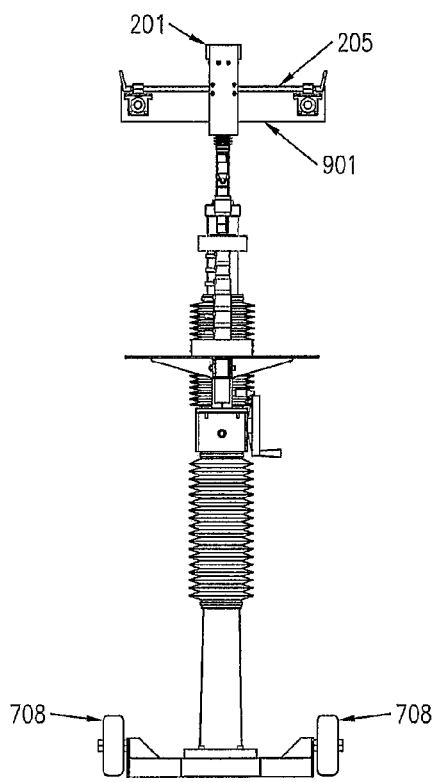
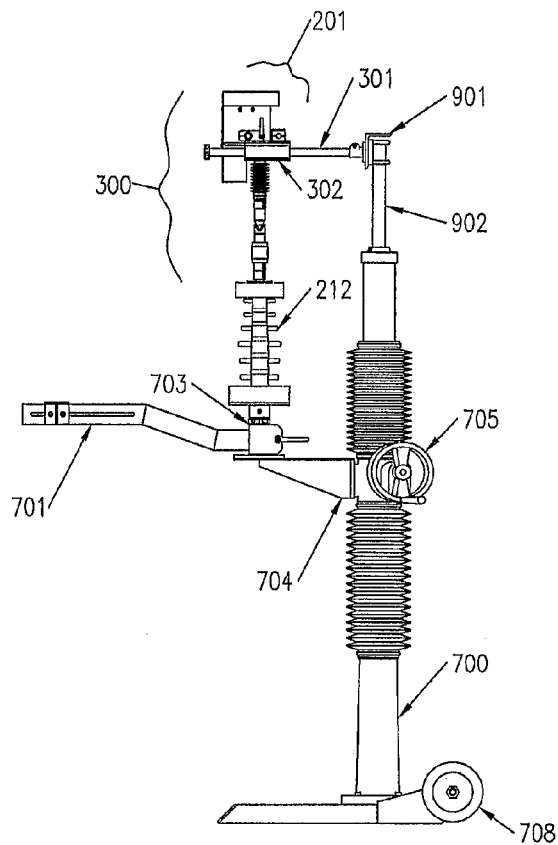
FIG.9C
FIG.9A
FIG.9B

SIMPLIFIED SPINE TESTING DEVICE

BACKGROUND OF THE INVENTION

1. Field of the Invention

The present invention relates to materials testing and, more particularly, to bio-medical and bio-materials testing and motion studies of cadaveric spinal specimens, functional spinal units (FSU), simulated spine models and spinal constructs. Though the primary application is for spine testing, the present invention may also be useful in testing other biological units for which unconstrained physiological loading is important, including, but not limited to, ankles, knees, wrists, feet, and hands.

2. Description of Related Art

The field of materials testing related to biomaterials and biomedical products has seen significant growth in recent years. Current materials test systems employed in the field of spinal research have become extremely complex and expensive.

Typical specimens or articles to be tested include cadaveric spines or sections thereof; an FSU; simulated spine models; or spinal constructs. The most basic specimen would typically be a cadaveric spine or simulated FSU as shown in FIG. 1.

An FSU is also known as a single motion segment of the spine which is the smallest physiological motion segment to exhibit similar biomechanical characteristics to those of the entire spine. An FSU includes two adjacent vertebrae (100) and the intervertebral disc (101) along with all of the adjoining ligaments between them (not shown in FIG. 1 for clarity). The FSU would exclude all of the connecting musculature. The vertebrae have anterior and posterior surfaces. The posterior surface is identified by the central location of the spinous process (not shown) and the transverse process (102) which extends laterally from the posterior half of the vertebra. FIG. 1 shows the three anatomical axes, X, Y, and Z, which converge at the vertebra. The X axis represents the horizontal axis about which lateral bending occurs, the Y axis represents the horizontal axis about which flexion and extension occurs, and the Z axis represents the vertical axis about which axial rotation occurs. The FSU shown in FIG. 1 is capable of six degrees of freedom, namely, translation along each of the axes (X, Y, and Z) and rotation about each of those axes.

A majority of currently available commercial and non-commercial automated test systems used for spinal testing attach to the top of the specimen and affix the bottom of the specimen through the use of some type of attachment point or clamping mechanism. Through the use of multiple motors and computer control systems, the test systems attempt to replicate in vivo motion. While some complex test systems may come close to achieving this goal, most do not because they produce motion through constrained attachment and programmed control which "moves the spine where the machine wants to move it".

SUMMARY OF THE INVENTION

The most realistic spinal testing thus far has been produced in non-commercial, non-automated test stands via the use of free weights applying loading about the various axes in a relatively unconstrained manner.

Disclosed herein are sample testing systems that can substantially duplicate "free weight" loading by way of a simple drive mechanism and a control system operating under the control of control software to apply torsion to the various axes while allowing the spinal specimen to "move where it wants to move". The sample testing systems disclosed herein allow for automated and continuous loading of the spinal specimen through a range of motion (i.e., back and forth through zero load to either positive or negative moments). Advantages of this automated continuous mode of loading include, but are not limited to: (1) application of physiological continuous loading as compared to step-wise loading; (2) control over the rate of continuous loading/displacement so as to respect the viscoelastic nature of the biological specimens; (3) ability to continuously acquire data (such as segment translations and rotations) from an external source such as a motion capture system without stopping the specimen test; (4) ability to test the specimen under displacement rate control to a specific rotation; (5) ability to test the specimen under load control to a specific moment; (6) ability to test the specimen under displacement rate control to a specific moment; (7) ability to test the specimen under load control to a specific rotation; (8) easy change of mode of testing while maintaining specimen alignment; and (9) reduction in time required for testing of a specimen due to the above advantages. The last advantage is particularly important for testing of fresh-frozen biological specimens, as time of testing is a significant factor in acquiring quality data.

In addition, because of the relatively small size of the loading mechanisms, the sample testing systems described herein also allows easier free access to the specimen. This is important in allowing users relatively unfettered access for application of transducers, in situ application of surgical procedures, easy access for radiographs/fluoroscopes, and manipulation of the specimen while in the test system.

Each sample testing system described herein includes a drive assembly to transmit torque to a test specimen. A mounting system for the drive assembly uses the reactionary force from the application of torque to the test specimen to allow the drive assembly to follow the natural movement of the spinal specimen as it bends and/or twists in response to applied torque.

More specifically, disclosed is a sample testing system comprising: a motor (401); a gear reducer (403, 405-407) coupled to the motor; a spline adapter (410) coupled to the motor via the gear reducer; a body (412) supporting the motor, the gear reducer and the spline adapter; a shaft (205) supporting the body (412) having the motor, the gear reducer and the spline adapter mounted thereto for linear motion on the shaft; and a ball spline shaft (422) supported by the spline adapter substantially perpendicular to an axis of the shaft (205) for rotation by the motor via the spline adapter and the gear reducer, wherein an end of the ball spline shaft opposite the spline adapter is coupleable to a sample under test.

The body can be adapted to move linearly on the shaft in response to rotation of the ball spline shaft via the motor and the gear reducer.

The spline adapter and the ball spline shaft are desirably adapted to enable translation of the ball spline shaft linearly along its axis during rotation of the ball spline shaft via the motor and the gear reducer.

The gear reducer can include: a planetary gear reducer, a pair of pulleys coupled by a belt, or both.

A pair of bearing blocks (302) can be coupled to opposite ends of the shaft (205) for linear motion to a pair of linear shafts (301) having axes disposed substantially perpendicular to the axis of the shaft (205).

An axis of the ball spine shaft (422) is desirably disposed substantially parallel or substantially perpendicular with axes of the pair of linear shafts (301) and substantially perpendicular to the axis of the shaft (205).

The sample testing system can further include: a mounting arm (701); and a pair of columns (202) coupled between the shaft (205) and the mounting arm.

The mounting arm can be pivotally coupled to a table (704).

Also disclosed herein is a sample testing system comprising: a motor (401); a gear reducer (403, 405-407, 1107); an output shaft (422, 1110) coupled for rotation by the motor via the gear reducer; a first device (413, 1103) adapted to enable the output shaft (422) to move linearly in a first direction substantially parallel with an axis of the output shaft; and a second device (205/412, 1104 or 1105) coupled to the first device for enabling the output shaft (422) to move linearly in a second direction substantially perpendicular to the first direction.

The sample testing system can further include a third device (301/302, 1104 or 1105) coupled to the first and second devices for enabling the output shaft (422, 1110) to translate linearly in a third direction substantially perpendicular to the first and second directions.

The first device can be one of the following: a linear slide assembly (1103); or a ball spline (413) supporting the output shaft (422) for linear translation thereof. The output shaft (422) can be a spline shaft.

The second device can be one of the following: a linear slide assembly (1104 or 1105); or a body (412) supported by a shaft (205) for linear motion thereon, wherein the motor, the gear reducer, and the output shaft are mounted to the body.

The third device can be one of the following: a linear slide assembly (1104 or 1105); or one or more shafts (301), each of which is coupled to the output shaft (422) via a bearing block (302).

Lastly disclosed herein is a sample testing device comprising: a multi-axis motion assembly (1103, 1104 and 1105); a motor (401) supported by the multi-axis motion assembly; a gear reducer (1107) supported by the multi-axis motion assembly; and an output shaft (1110) coupled for rotation by the motor via the gear reducer, wherein the multi-axis motion assembly is adapted to enable the combination of the motor, the gear reducer and the output shaft to move in substantially perpendicular directions, including a direction parallel with an axis of the output shaft, when the output shaft is rotatably driven by the motor via the gear reducer.

The multi-axis motion assembly can include a plurality of linear slide assemblies coupled together such that the plurality of linear slide assemblies are moveable in substantially perpendicular directions to each other.

The multi-axis motion assembly can be adapted to enable the combination of the motor, the gear reducer and the output shaft to move in three perpendicular directions.

The sample testing device can further include a device for coupling the output shaft to a sample under test and/or a device for repositioning the output shaft axis relative to the sample under test.

BRIEF DESCRIPTION OF THE DRAWINGS

FIGS. 6A, 6B, and 6C are different side views of the drive assembly of FIGS. 2A-2B showing its ability to align (tilt) about the shaft (205) in response to the drive assembly applying torque to the specimen (not shown) during bend testing, wherein FIG. 6B shows the drive assembly in an expected starting position for bend testing;

FIGS. 9A, 9B and 9C are respective front, side, and top views of the vertical drive mounting assembly of FIGS. 3A-3B on a test stand for use in torsion testing thru the Z axis of the spinal specimen;

FIGS. 15A and 15B are different top views of an embodiment of the self-contained test stand of FIGS. 14A-14C, wherein FIG. 15A shows a top slide assembly and vertically mounted drive assembly above a specimen (not specifically shown) and rotating 90° to facilitate bend testing of the spinal specimen, and wherein FIG. 15B shows a bend testing slide assembly and horizontally mounted drive assembly coupled to a post that facilitates pivoting of the horizontally mounted drive assembly around the spinal specimen (not specifically shown);

DETAILED DESCRIPTION OF THE INVENTION

Figure 1:
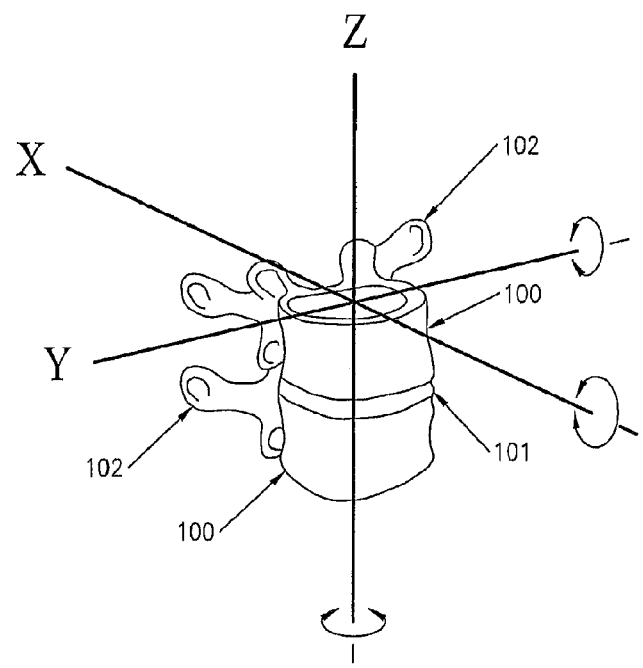
FIG. 1 is a view of a ligamentous spinal motion segment (a spinal specimen), also known as a functional spinal unit (FSU), showing the anatomical parts and multiple axes about which a sample testing device can apply torsion.
Figure 2B:
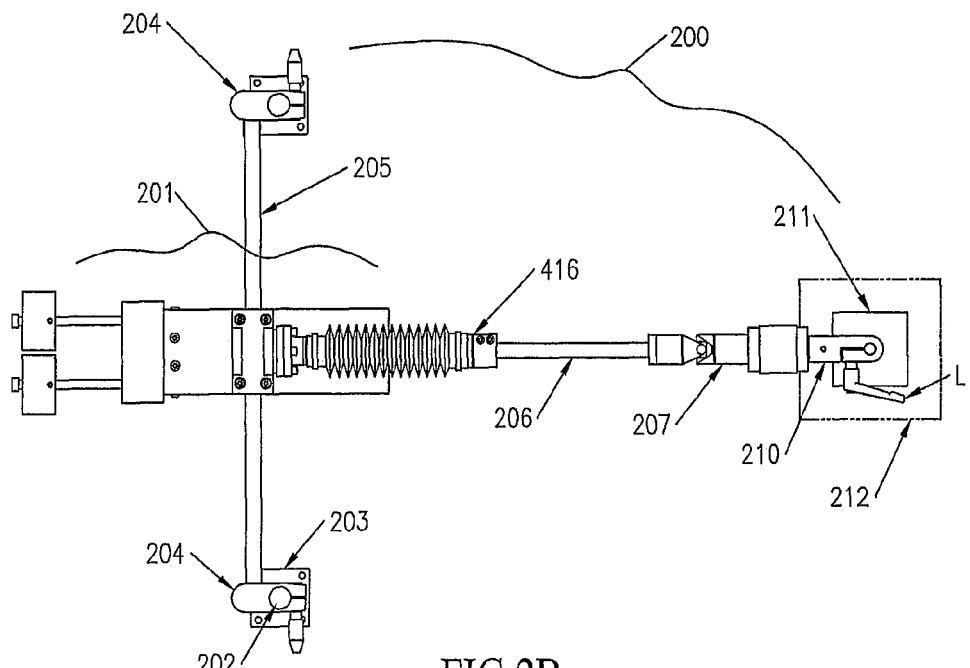
FIGS. 2A and 2B are respective side and top views of an embodiment of a sample testing device including a drive assembly and mounting components comprising a horizontal drive mounting assembly attached to a spinal specimen for flexion-extension or lateral bend testing thereof.
Figure 2A:
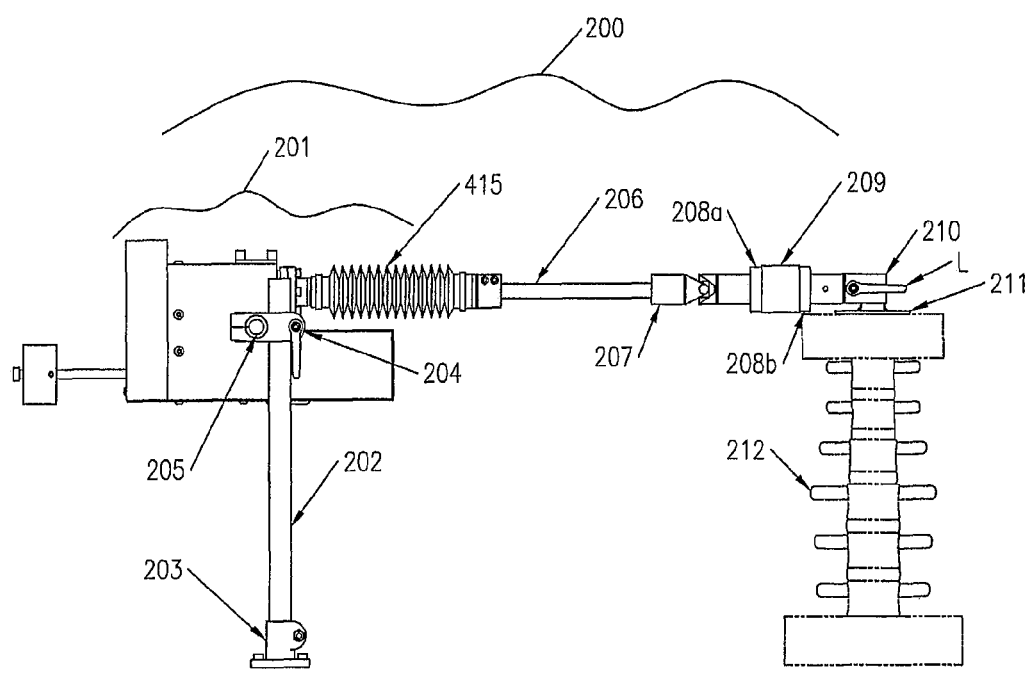

Referring to FIGS. 2A-2B, FIG. 2A is a side view of a sample testing device that includes a drive assembly (201) and miscellaneous parts that comprise a horizontal drive mounting assembly (200) and FIG. 2B is a top view of the same. A representation of a spinal specimen (212) is shown throughout this document for simplicity but the spinal specimen (212) can be any of the previously discussed specimens, such as the FSU shown in FIG. 1, or a spinal construct.

Drive assembly (201) shown in FIGS. 2A-2B is in a horizontal orientation for flexion/extension and lateral bend testing. Two support columns (202) are held in an upright position by respective foot mounting brackets (203). Near the top of each support column (202) is a quick release column clamp (204) which is used to hold a linear shaft (205) in a desired location, desirably horizontal or substantially horizontal. Column clamps (204) allow adjustment of the overall height of shaft (205) and, hence, drive assembly (201) mounted on shaft (205) to accommodate spinal specimens of differing heights.

Attached to a shaft adapter coupling (416) coupled to drive assembly (201) is a drive shaft (206) which extends horizontally (or substantially horizontally) to an alignment coupling (207) which in-turn, is attached to a specimen clamp (210) via a reaction torque transducer (209) which is sandwiched between adapter plates (208a and 208b). Clamp (210) shown in FIGS. 2A-2B is but one means for attachment to test specimen (212) and is, therefore, not to be construed as limiting the invention. In the embodiment of clamping device (210) shown in FIGS. 2A-2B, a round or rectangular specimen mounting plate (211) is affixed to the top of spinal specimen (212). A round pin (not shown) extends vertically from plate (211). Clamping device (210) slips over this pin and is tightened by way of a lever L. This allows for ease of attachment to test specimens (212) which can increase test throughput.

Figure 3B:
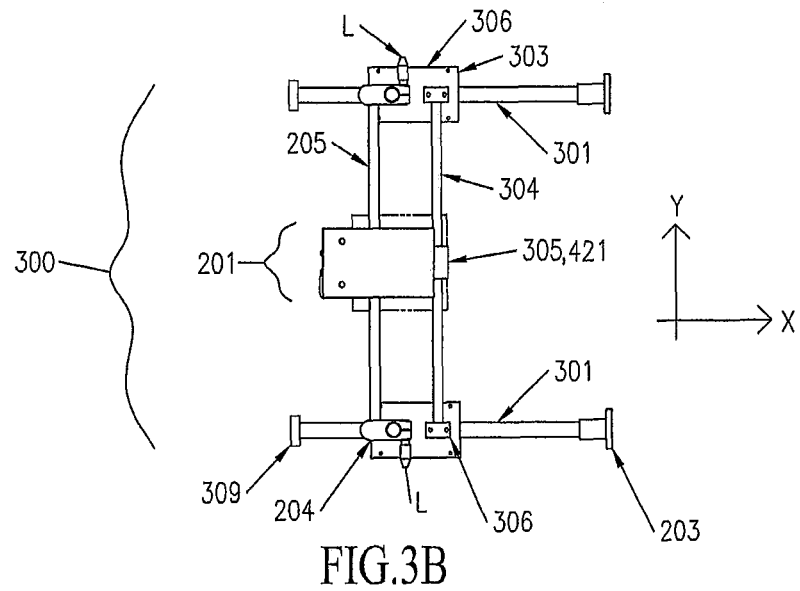
FIGS. 3A and 3B are respective side and top views of an embodiment sample testing device including a drive assembly and mounting components comprising a vertical drive mounting assembly attached to a spinal specimen for axial rotational testing about the Z axis thereof.
Figure 3A:
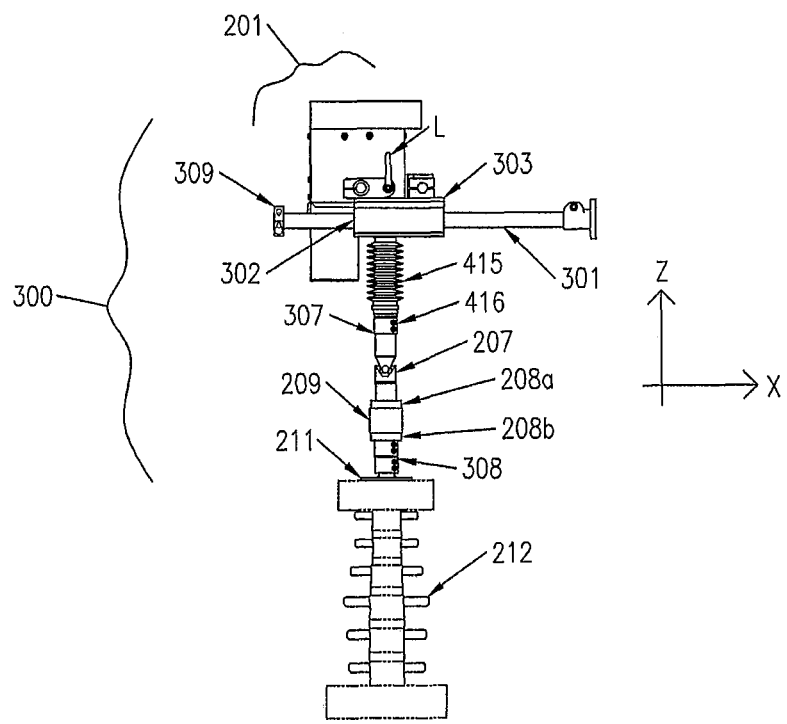

Often, spinal test protocols include testing performed by applying torsion (or torque) about (or around) the Z axis of specimen (212) (shown in FIG. 1). To accommodate this type of testing, drive assembly (201) can be mounted in a vertical orientation as shown in FIGS. 3A and 3B. Additional parts as needed can be pre-mounted to a test frame provided with drive assembly (201) (see, e.g., FIGS. 7, 8, 9—discussed hereinafter) or the additional parts can be installed by the user in a manner they see fit when test protocols require changing tests from bending to torsion, or vice versa, for example. Changing drive assembly (201) between a horizontal testing position and a vertical testing position can be straightforward and requires little time, especially if the required parts are pre-mounted.

FIG. 3A is a side view of a sample testing device that includes drive assembly (201) and mounting component comprising a vertical drive mounting assembly (300) and FIG. 3B is a top view of the same. Two parallel horizontal linear shafts (301) are affixed to a vertical surface (not shown) via foot mounting brackets (203). Mounted on these shafts (301) are linear bearing blocks (302). Each bearing block (302) includes one or more, desirably two, linear bearings. Adapter plates (303) are mounted on the top surface of bearing blocks (302). Shafts (301) and bearing blocks (302) provide for one axis of movement of drive assembly (201) once installed.

A precision linear shaft (304) has a linear bearing housing (305) including a linear bearing pre-installed thereon. This shaft (304) includes shaft clamps (306) at opposite ends coupled to pins on adapter plates (303). Once shaft (304) is in place and positioned at a 90° angle to shafts (301), shaft clamps (306) are secured in place. Bearing housing (305) can be moved or translated on shaft (304) as needed to keep it out of the way during installation or change over of a spinal specimen (212).

Drive assembly (201) together with horizontal linear shaft (205) and the two quick release clamps (204) described in FIGS. 2A-2B, can be placed over pins located on adapter plates (303) and clamped in place using locking levers L. Bearing housing (305) can then be aligned with a bearing mount (421) and fastened in place, thereby effectively locking out the ability of the drive assembly (201) to tilt, creating an X-Y slide feature for drive assembly (201).

A short drive shaft (307) is coupled at one end to drive assembly (201) via a shaft adapter coupling (416) and is attached at its opposite end to alignment coupling (207). Attached to the alignment coupling (207) is reaction torque transducer (209) sandwiched between adapter plates (208a and 208b) pre-installed. Adapter plate (208b) nearest spinal specimen (212) is clamped to a split shaft collar (308) which in turn is clamped to specimen mounting plate (211) that has been affixed to the top surface of spinal specimen (212).

This arrangement allows drive assembly (201) to transfer torsion (or rotational torque) about or around the Z axis of spinal specimen (212). The XY feature of the mounting assembly together with a ball spline (413) (shown in FIG. 4A) and alignment coupling (207) enables drive assembly (201) to follow natural movements of the spine specimen (212) as torque is applied.

Heretofore, drive assembly (201) has been described generally as it has related to various mounting arrangements. Drive assembly (201) will now be described in detail.

Figure 4B:
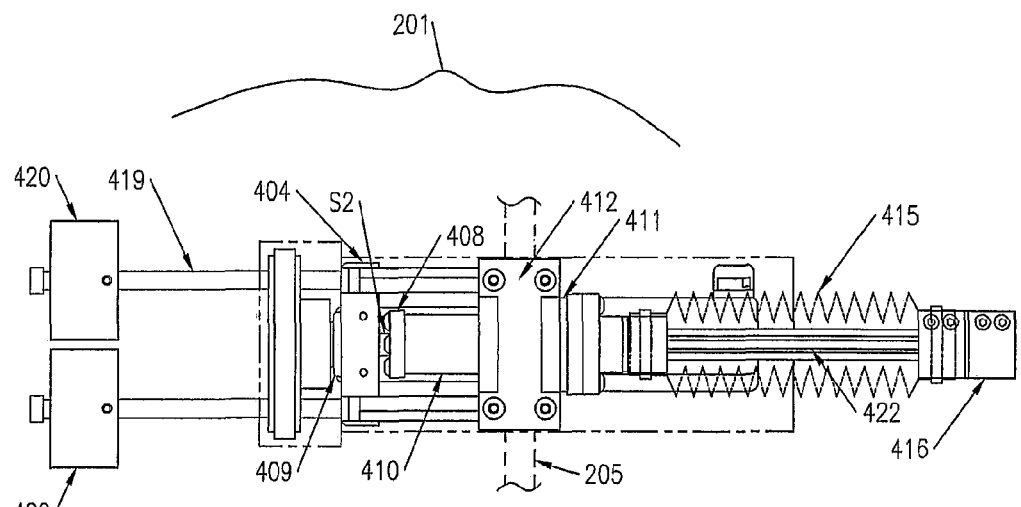
FIGS. 4A and 4B are respective side and top views of the drive assembly shown in FIGS. 2A-2B with its protective cover shown in phantom to better show the individual component parts thereof.
Figure 4A:
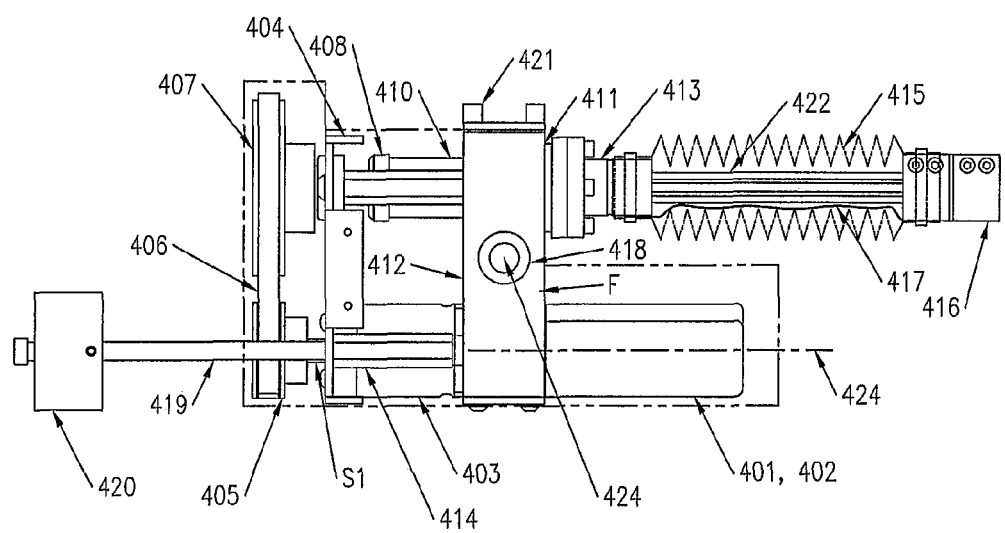

FIGS. 4A and 4B show side and top views of drive assembly (201) with an outline of the cover thereof shown in phantom lines. Desirably, drive assembly (201) is made from lightweight materials where possible and compact packaging of components for ease of mounting and/or change-over from vertical to horizontal testing, or vice versa.

A main body (412) of drive assembly (201) is a machined aluminum block to which all other components are attached. Four stand-offs (414) are attached to main body (412) at one end and at opposite ends to a rear mounting plate (404). Main body (412) and mounting plate (404) are used to support and position drive train components of drive assembly (201).

The drive train components of drive assembly (201) include a servo-motor (401), having an integral rotary encoder (402), coupled to an inline planetary gear reducer (403) which is fastened to rear mounting plate (404). Gear reduction by planetary gear reducer (403) is via a two-stage gear set yielding a reduction ratio of 25:1. An output shaft (S1) of gear reducer (403) attaches to a timing belt pulley (405). In one non-limiting embodiment, pulley (405) is a 5 mm pitch pulley with 24 grooves. Pulley (405) is connected by a timing belt (406) to a driven pulley (407), desirably of the same pitch as pulley (405) but with 48 grooves. This belt and pulley arrangement yields a secondary reduction ratio of 2:1 for an overall speed reduction of 50:1 from the output shaft of servo-motor (401) to driven pulley (407).

Driven pulley (407) is attached to a shaft S2 of a pulley adapter (408). Shaft S2 passes through and is supported by a bushing (409) which is mounted near the top of rear mounting plate (404). A flanged bushing (411) is press-fit into main body (412) with a flange of flanged bushing (411) resting against a front (F) of main body (412). A spline adapter (410) passes through and is supported by bushing (411) with a flange of spine adapter (410) resting against the flange of the bushing (411). An end of spline adapter (410) opposite bushing (411) is attached to pulley adapter (408). By way of this arrangement, pulley adapter (408) and spline adapter (410) are rotatable in response to rotation of driven pulley (407).

A ball spline (413) includes an internal flanged recirculating linear ball bushing (not shown) and a matching grooved linear ball spline shaft (422), as is known in the art. At the front (F) of main body (412) a flanged surface of ball spline (413) is attached to the flange of spline adapter (410). This assembly enables ball spline shaft (422) to move linearly in and out of spline adapter (410) while transmitting rotary motion. Spline adapter (410) and ball spline (413), including ball spline shaft (422), are components known in the art and, therefore, will not be described in greater detail herein for simplicity.

Extending from and attaching to ball spline (413) is a flexible bellows (415) that extends and attaches at its opposite end to a shaft adapter coupling (416). Flexible bellows (415) protects ball spline shaft (422) from contamination while allowing linear and rotary motion of ball spline shaft (422). Inside bellows (415), a flexible cable (417) attached between spline adapter (410) and shaft adapter coupling (416) is used to retain ball spline shaft (422) and limit its axial travel.

Main body (412) includes a bore (424) passing from side to side, perpendicular to an axis of ball spline shaft (422). Bore (424) is located approximately midway between an axis (424) of motor (401) and an axis of ball spline shaft (422). This location of bore (424) keeps the heaviest components below a center-of-gravity of the drive assembly (201) and allows for better balance. Located at each end of bore (424) is a self-aligning precision linear ball bushing (418). The purpose of bushings (418) is to allow for reduced friction linear travel of drive assembly (201) on horizontal linear shaft (205), as shown in FIGS. 2B, 4B (in phantom), and 5. Bushings (418) also enable drive assembly (201) to tilt when mounted for horizontal testing as shown in FIGS. 2A-2B. Tilting of drive assembly (201) is shown in FIGS. 6A, 6B, and 6C.

Attached to and extending from the rear of the drive assembly (201) when mounted for horizontal testing are two long shoulder bolts (419) supporting counterweight (420). Counterweights (420) are used to balance drive assembly (201) substantially horizontally when it is mounted on horizontal linear shaft (205). Counterweights (420) are positioned by manually moving them along the axes of shoulder bolts (419) and locking them in place via set screws. When drive assembly (201) is mounted for vertical use as shown in FIGS. 3A-3B, shoulder bolts (419) and counterweights (420) may be omitted since the balance and tilt feature is negated by the use of the second horizontal shaft (304) with its attached bearing housing (305) connected to the drive assembly (201) by way of bearing mount (421).

Drive assembly (201), shown in the horizontal drive mounting assembly (200) in FIGS. 2A-2B, uses horizontal linear shaft (205), which passes through two precision linear bearings (418) mounted within main body (412) of Drive Assembly (201), to travel or traverse on in response to bending of spinal specimen (212).

Figure 5:
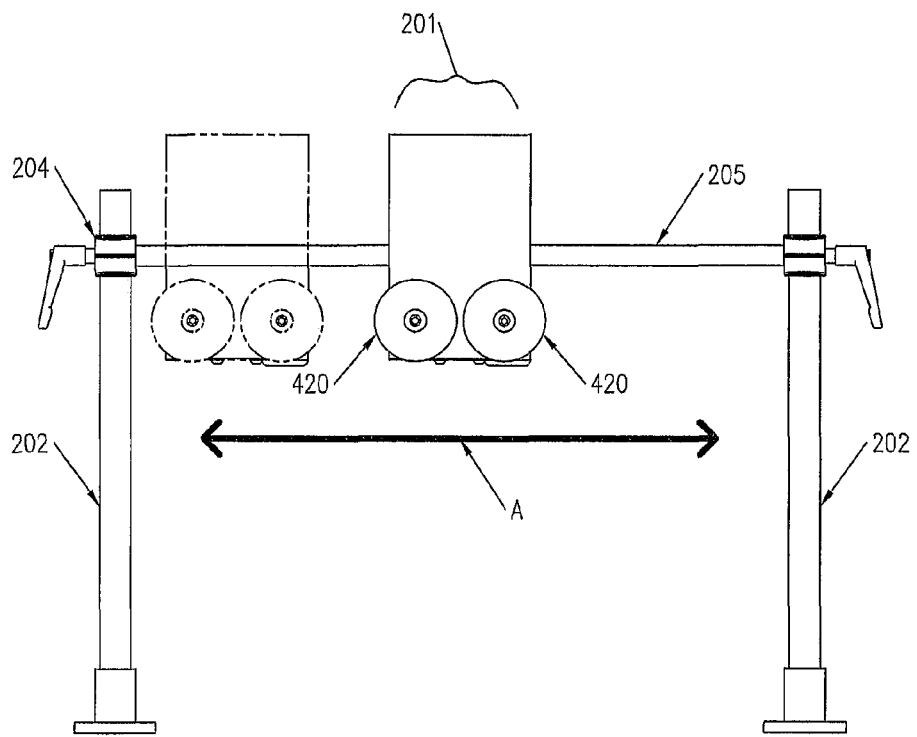
FIG. 5 is a rear view of the drive assembly shown in FIGS. 2A-2B at a neutral or central position on a shaft and a second, phantom position on the shaft shown to represent the motion of the drive assembly during bend testing.

FIG. 5 is a simplified rear view of the horizontal drive mounting assembly (200) showing the drive assembly (201) in its neutral or central position as would be the case when spinal specimen (212) is standing upright prior to bending. To the left of center, a rear view of the drive assembly (201) is shown in phantom lines to represent drive assembly (201) as it would move or translate to the left in FIG. 5 in response to the application of a counterclockwise torque to the top of spinal specimen (212). Arrow A in FIG. 5 indicates that the drive assembly (201) can move or translate on shaft (205) either right or left as necessary in response to torque being applied to spinal specimen (212). In use, shaft (205) is desirably level. Shaft (205) can be adjusted for height or level via quick release column clamps (204) mounted on upright support columns (202).

In addition to the linear travel of drive assembly (201) on shaft (205) discussed above, an additional degree of freedom is afforded by the use of linear shaft (205) and bearings (418). Specifically, drive assembly (201) has the ability to tilt about shaft (205) at the same time it moves or translates along the axis of shaft (205). FIGS. 6A, 6B, 6C illustrate drive assembly's (201) ability to tilt about shaft (205) in response to bending of spinal specimen (212) during testing. Alignment coupling (207) attached between drive shaft (206) and reaction torque transducer (209) allows for angular misalignment therebetween. While drive assembly (201) can follow these paths, ball spline shaft (422) can move or translate axially into or out of ball spline (413) via the recirculating linear ball bushing thereof as necessary, within the limits of the length of cable (417), to allow for unconstrained movement of spinal specimen (212) in multiple axes.

Advantages of drive assembly (201) include: simple design, light weight portability, and mounting versatility. When used in the horizontal drive mounting assembly (200) configuration, drive assembly (201) can be mounted to a table or bench top. When used in the vertical drive mounting assembly (300) configuration, drive assembly (201) can be mounted to a wall or any vertical surface providing sufficient support.

Figure 7C:
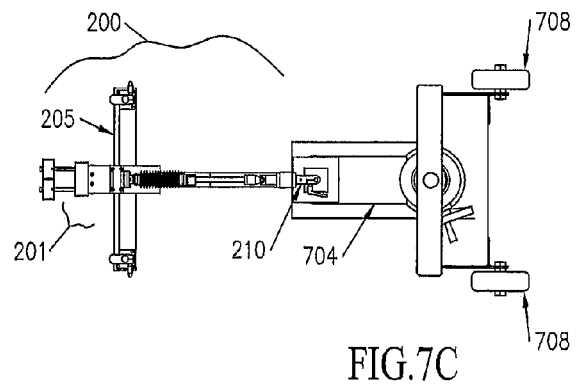
FIGS. 7A, 7B and 7C are respective front, side, and top views of the horizontal drive mounting assembly of FIGS. 2A-2B on a test stand for use in flexion-extension (or lateral) bend testing of a spinal specimen.
Figure 7A:
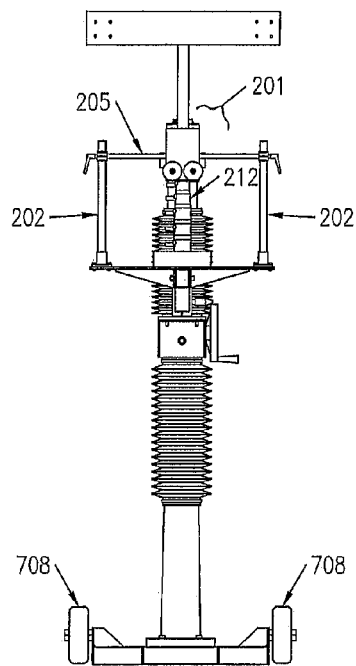
Figure 7B:
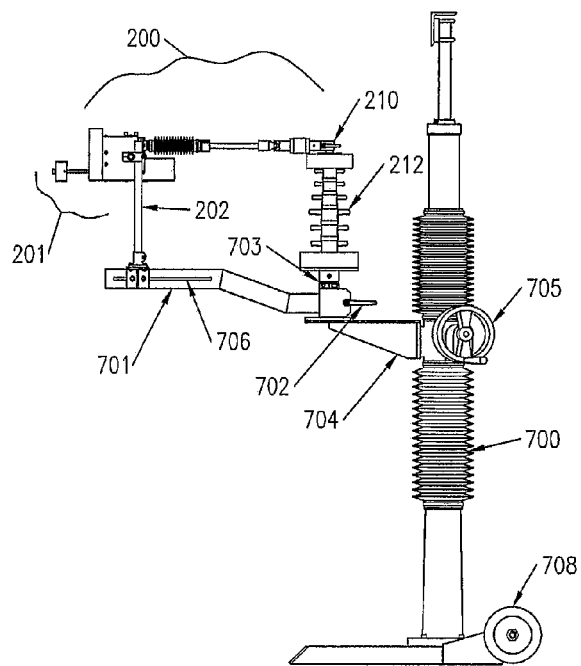

FIGS. 7A, 7B, 7C show respective front, side, and top views of the horizontal drive mounting assembly (200) mounted to an embodiment of a test stand (700). Test stand (700) includes a mounting arm (701) which provides adjustment of the drive assembly (201) in two planes, namely, horizontal and vertical planes. The distal end of mounting arm (701) includes a slot (706) which allows for adjustment of the position of drive assembly (201) and its associated horizontal mounting hardware closer to or out further away from spinal specimen (212). In addition, at the proximal end of arm (701) closest to specimen (212) there is a quick release clamp (702) that when loosened allows for rotation of mounting arm (701) about a specimen mounting post (703) (see FIG. 8). When clamp (210) is loosened at the top of the spinal specimen (212) and quick release clamp (702) is loosened at the specimen mounting post (703), the entire horizontal drive mounting assembly (200) can be quickly repositioned or rotated, e.g., rotated 90°, for change over from extension-flexion testing to lateral bending testing, or vice versa, to aid in testing efficiency. This mounting arrangement allows for both tests to be performed with no change in the position of spinal specimen (212).

Figure 8:
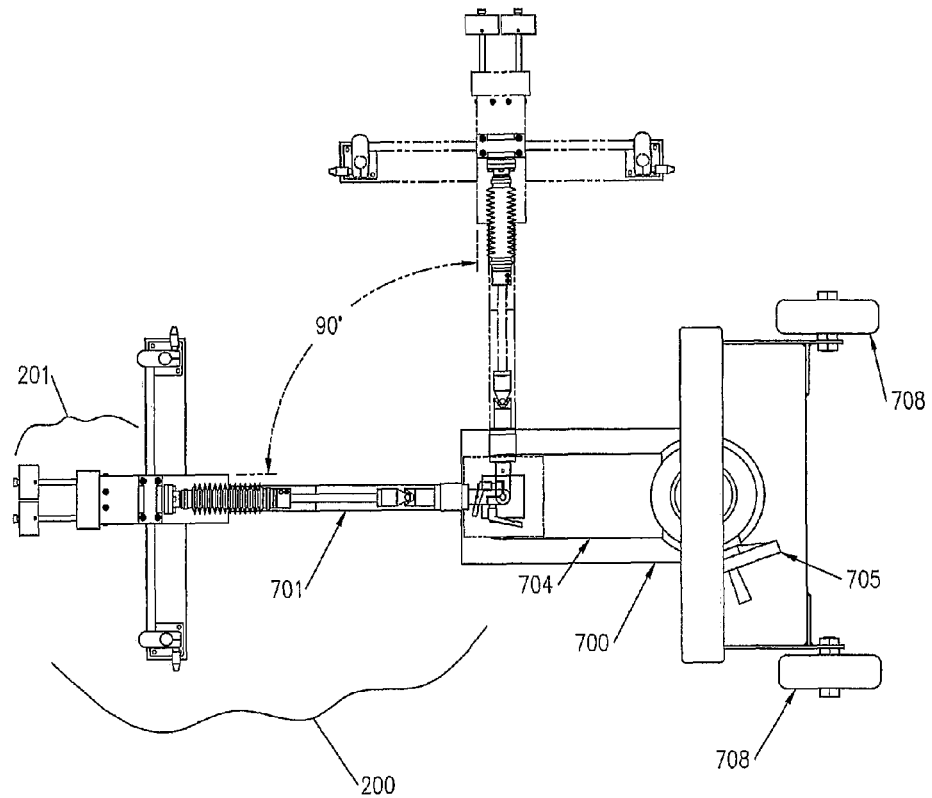
FIG. 8 is a top view of the horizontal drive mounting assembly of FIGS. 7A-7C illustrating repositioning of the horizontal drive mounting assembly without moving the spinal specimen to allow for change from flexion-extension (or lateral) bend testing to lateral (or flexion-extension) bend testing of the spinal specimen.

FIG. 8 is a top view of the horizontal drive mounting assembly (200) shown in FIGS. 7A-7C showing a 90° swing of arm (701). Arm (701) can be locked in any position within the arc indicated for special testing purposes. Another advantage of test stand (700) is the attachment to a table (704) which is vertically adjustable (up and down) by way of a hand-wheel (705) employing a rack and pinion set and a clamp locking mechanism. Test stand (700) may also be equipped with a dolly handle (not shown) and wheels (708) for ease of movement between locations.

With reference to FIGS. 9A-9C, the embodiment of test stand (700) in FIGS. 9A-9C is similar to test stand (700) in FIGS. 7A-7C with the exception that FIGS. 9A-9C show test stand (700) with the vertical drive mounting assembly (300) installed for torsion testing about the Z axis of a spinal specimen (212). Features of test stand (700) in FIGS. 9A-9C not previously discussed in connection with test stand (700) in FIGS. 7A-7C include the ability to mount vertical drive mounting assembly (300) to a pre-drilled crossbar (901) at the top of test stand (700). Crossbar (901) is mounted to an upright post (902) which is manually adjustable for height so as to adjust the distance between drive assembly (201) and the top of the specimen (212) as well as to adjust the overall height of drive assembly (201) relative to vertically adjustable table (704) where specimen mounting post (703) is installed. Horizontal mounting arm (701) can be rotated as desired to a position that is out of way and clamped in place so as not to interfere with personnel conducting torsion testing of spinal specimen (212).

Figure 10:
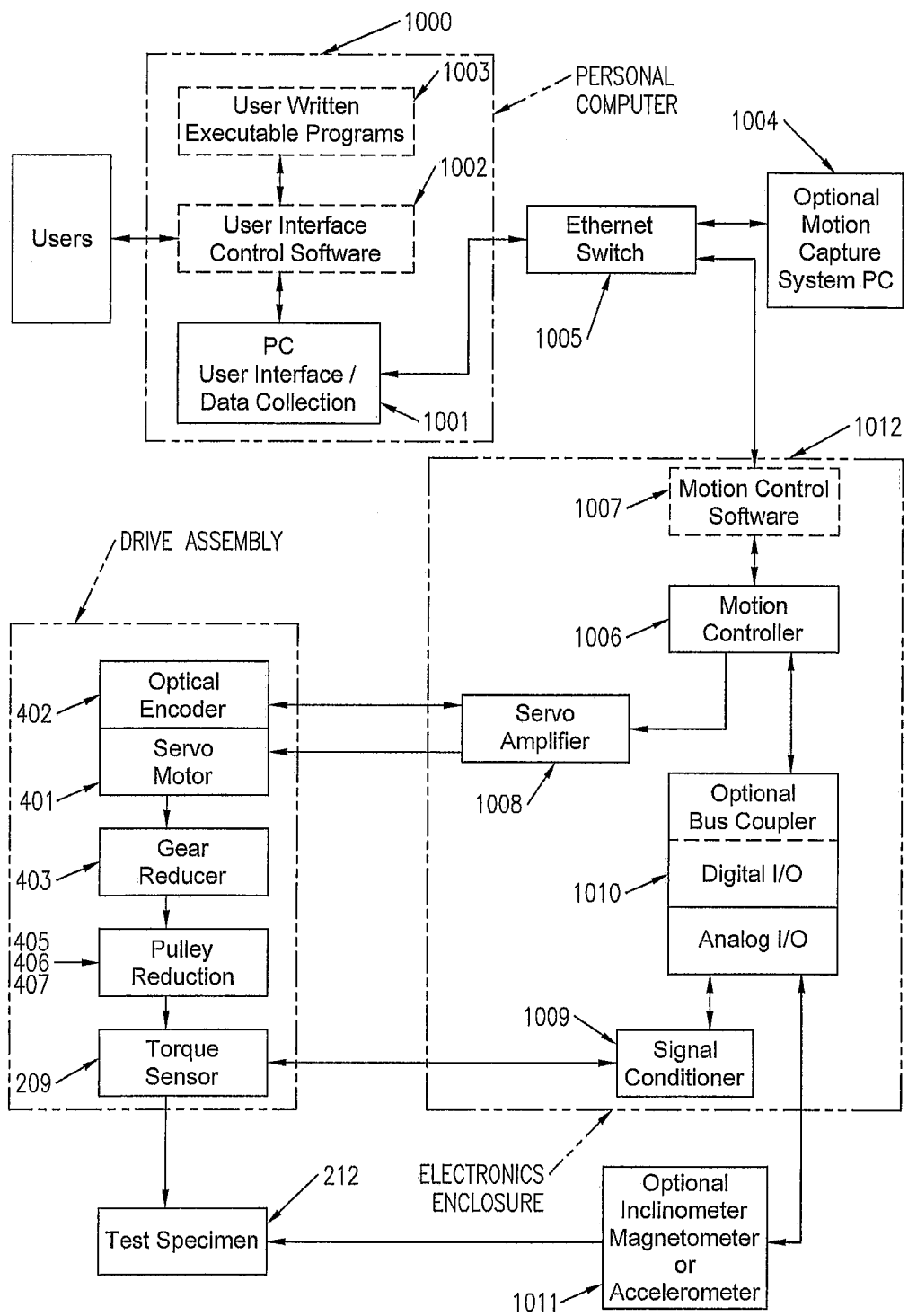
FIG. 10 is a block diagram of a control and data acquisition system that can be utilized with any embodiment drive mounting assembly of FIGS. 2A-2B or FIGS. 3A-3B for multiple testing modes.

With reference to FIG. 10, main control functions of drive assembly 200 and/or 300 are under the control of a personal computer (PC) (1000) running under the control of a control software program (1002) and a user interface (1001) written in suitable programming language, such as Visual Basic. Via PC (1000), a user can perform basic moves for test set-ups or write executable programs (1003) for performing specific tests and data collection. PC (1000) can store all system parameters, and can store specimen test programs and test data if instructed to do so. PC (1000) connects to all of the control hardware inside of an electronics enclosure (1012) via an Ethernet cable. PC (1000) can also be interfaced with an optional precision motion capture system (1004). If this latter option is used, an Ethernet cable connects PC (1000) to an Ethernet switch (1005) which then connects through Ethernet cables to the optional motion capture system (1004) and the electronics enclosure (1012).

Electronics enclosure (1012) houses a motion controller (1006) operating under the control of an embedded control program (1007) which is customized for the application. This program (1007) is used for motion sub-routines which are communicated to and from control software (1002) residing within PC (1000). A communications protocol known as Modbus TCP/IP can be used for this communication. Motion controller (1006) can use a field bus protocol to communicate with all system inputs, outputs, and a servo-amplifier (1008). The output of rotary encoder (402), which can be built into servo-motor (401), generates signals which feed into servo amplifier (1008). Encoder (402) is used to provide angular position feedback. If motion capture system (1004) is not used, an accurate angular position feedback signal may be attained by directly attaching an optional accelerometer, magnetometer, or inclinometer (1011) to spinal specimen (212).

The output of torque transducer (209) passes through a signal conditioner (1009) before being used for feedback control of torque being applied to spinal specimen (212). Torque transducer (209) is used to provide torsion feedback. Control Software (1002) allows specimen tests to be controlled by angular position or torque feedback in an operator based test program.

The previously described motion capture system (1004) can be used to gather three dimensional position data from markers attached directly to spinal specimen (212). An embodiment of this system, known by the trade name Optotrak®, in use by many spinal research laboratories, was developed by Northern Digital Inc. (NDI) of Waterloo, Ontario, Canada. Optotrak® is a registered trademark in the U.S. of Northern Digital Inc. of Waterloo, Ontario, Canada. Motion capture system (1004) can interface with PC (1000) using a protocol called Visual 3D/RT which communicates over an Ethernet connection.

Figure 11B:
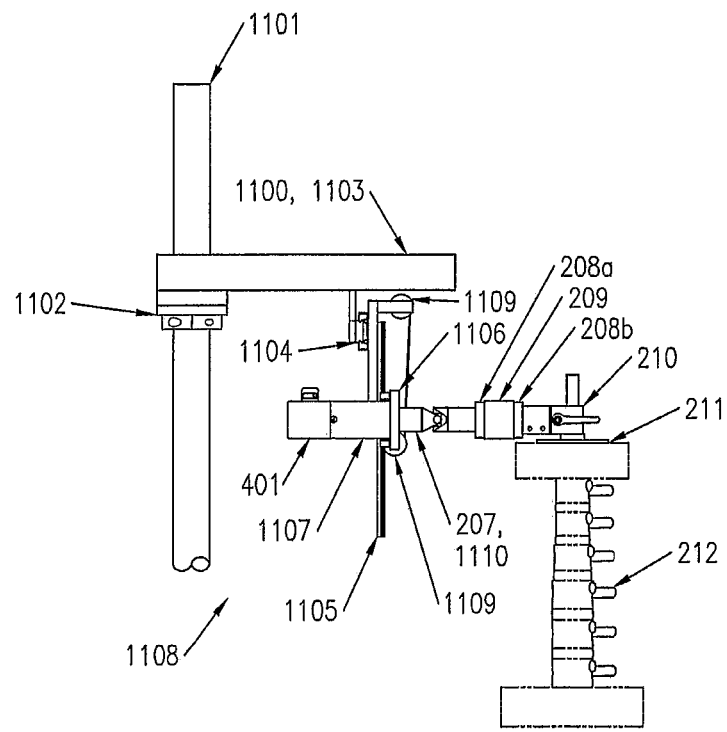
FIGS. 11A and 11B are respective front and side views of an embodiment of a sample testing device including a drive assembly and mounting components comprising a horizontal drive mounting assembly attached to a spinal specimen for flexion-extension or lateral bend testing thereof.
Figure 11A:
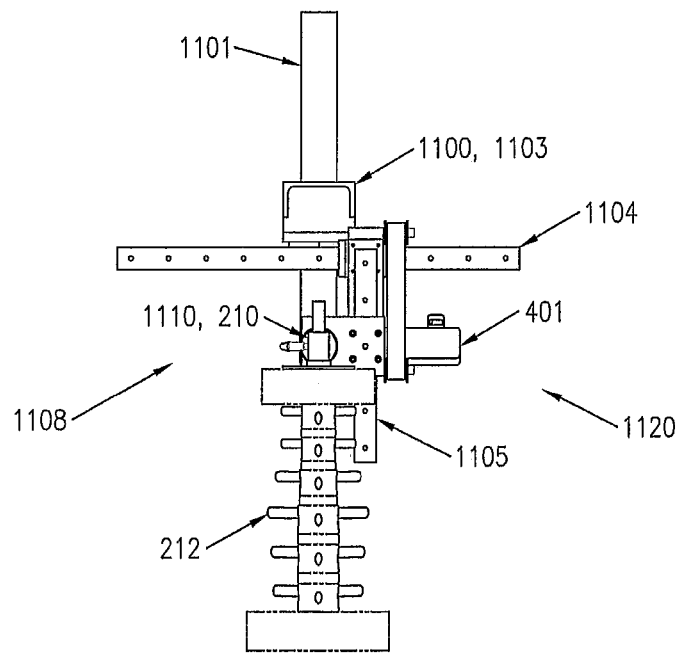

With reference to FIGS. 11A-11B, another embodiment horizontal drive mounting arrangement (1108) is shown in position to perform flexion/extension and lateral bend testing in much the same way as the horizontal drive mounting arrangement (200) shown in FIGS. 2A-2B. Horizontal drive mounting arrangement (1108) includes a horizontal arm (1100) mounted to a vertical column (1101) via a locking collar (1102) which allows for adjusting a height of horizontal arm (1100) to accommodate spinal specimens (212) of various sizes. Attached to an underside of horizontal arm (1100) is a linear slide assembly (1103) which runs parallel to an axis of horizontal arm (1100) and provides guidance in the X (or Y) axis of spinal specimen (212). Attached to slide assembly (1103) via a bracket is another linear slide assembly (1104) in the horizontal plane. This linear slide assembly (1104) provides guidance along the Y (or X) axis in a plane 90° from horizontal arm (1100).

Linear slide assembly (1104) is connected via a bracket to a third linear slide assembly (1105) that is mounted vertically and which supports a drive mounting bracket (1106). Drive mounting bracket (1106) is the attachment point for a drive assembly comprised of a right angle gear reducer (1107) that is attached to drive mounting bracket (1106) which supports servo-motor (401). A constant force spring and two pulleys (1109) provide for a counterbalance to right angle gear reducer (1107), servo-motor (401) and its associated parts.

Slide assemblies 1103, 1104 and 1105 and their related parts together define a multi-axis motion assembly 1120. The use of slide assemblies 1103, 1104 and 1105 disposed at right angles to each other can obviate the need for ball spine (413) and ball spline shaft (422) discussed above. However, this is not to be construed as limiting the invention.

Attached to an output shaft (1110) of gear reducer (1107) is alignment coupling (207) which then attaches to clamping device (210) via torque transducer (209) sandwiched between adapter plates (208a and 208b). Clamping device (210) is but one embodiment of a means to attach to spinal specimen (212). In this embodiment, round or rectangular specimen mounting plate (211) is affixed to the top of spinal specimen (212) with mechanical fasteners. A pin (not shown) extends vertically from mounting plate (211). Clamping device (210) slips over this pin and is tightened thereto by the use of a lever mechanism or fasteners. The combination of clamping device (210) and mounting plate (211) allows for ease of attachment to test specimens (212) which can increase test throughput and also provide for fast conversion from lateral bending tests to flexion/extension tests, or vice versa.

As discussed above, spinal test protocols often include testing performed by applying torsion about the Z axis of the specimen (212). To accommodate this type of testing, a suitable drive assembly can be mounted in a vertical orientation as well as horizontally. Additional parts as necessary can be pre-mounted to a test frame or the drive assembly can be installed in a desirable manner when test protocols require changing from bending to torsion tests, for example. Changing the orientation of the drive assembly from horizontal to vertical, or vice versa, can be straightforward and requires little time, especially when the required parts are pre-mounted.

Figure 12B:
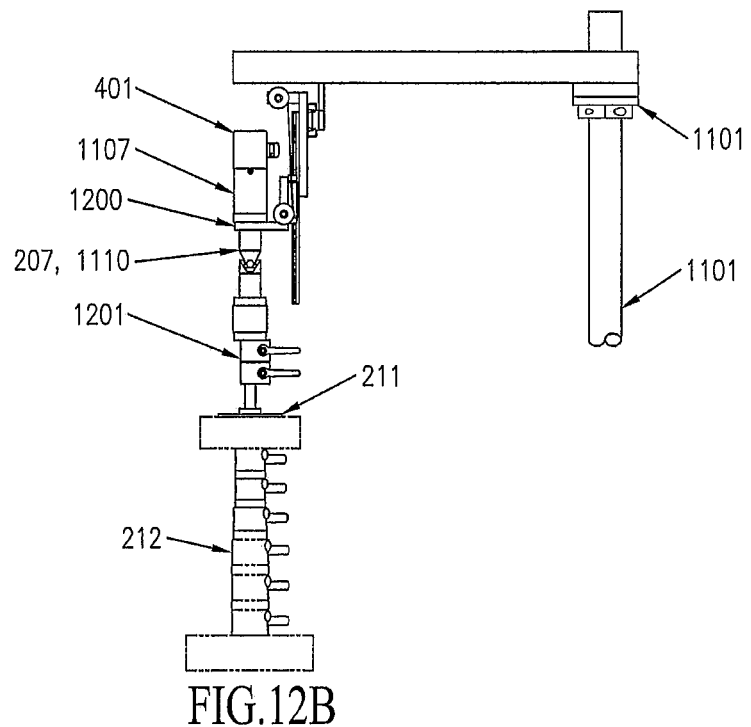
FIGS. 12A and 12B are respective front and side views of an embodiment of a sample testing device including a drive assembly and mounting components comprising a vertical drive mounting assembly attached to a spinal specimen for axial rotational testing about the Z axis thereof.
Figure 12A:
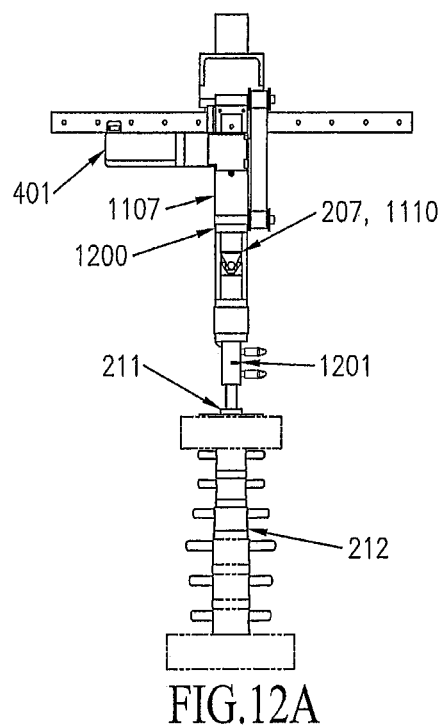

FIGS. 12A-12B illustrate another embodiment of a vertical drive mounting arrangement that includes motor (401) and gear reducer (1107) oriented to apply torsion around the Z axis of spinal specimen (212). All of the parts for this mounting arrangement are common to previously discussed horizontal drive mounting arrangement (1108) except for the addition of a mounting bracket (1200) to convert the orientation of gear reducer (1107) and drive motor (401) from the X or Y axis to the Z axis. Connection of motor (401) and gear reducer (1107) to spinal specimen (212) is through the use of a vertically oriented clamp mechanism (1201) attached to specimen mounting plate (211) which in-turn is attached to the top of spinal specimen (212).

Figure 13B:
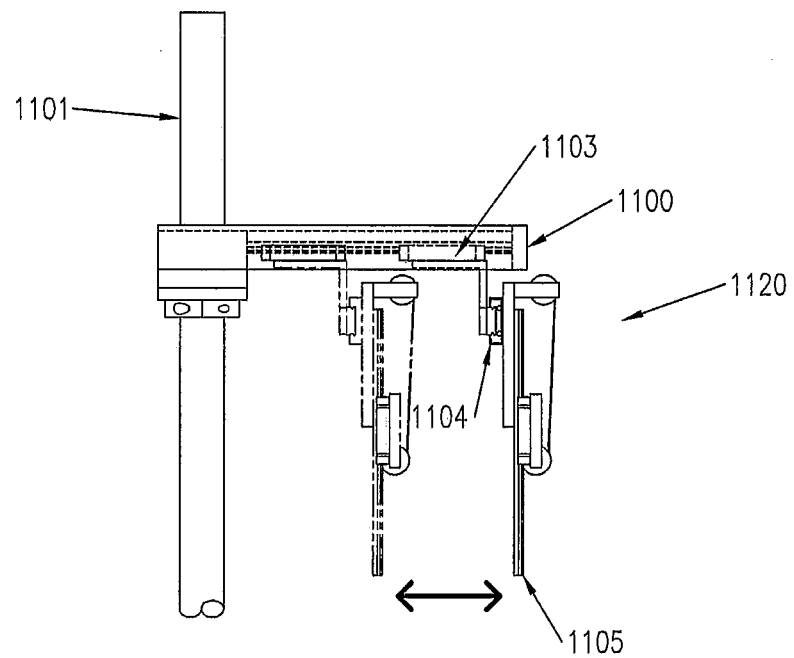
FIGS. 13A and 13B are respective isolated front and side views of the multi-axis linear slide assembly shown in FIGS. 11A-11B and FIGS. 12A-12B (with drive assembly omitted) that can be used for either horizontal or vertical placement of the drive assembly.
Figure 13A:
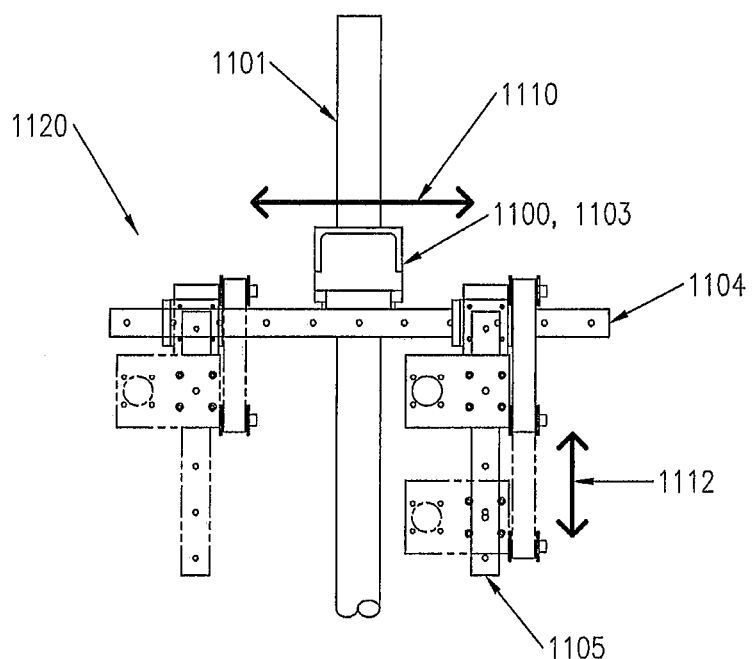

FIG. 13A is an isolated front view of multi-axis motion assembly (1120) of FIGS. 11A-11B. This figure shows linear slide assemblies (1104 and 1105) and arrows (1110 and 1112) indicating the direction of movement for each. Horizontally mounted linear slide assembly (1104) allows for X (or Y) axis travel depending on the orientation of the spinal specimen (212), while the shorter vertically mounted linear slide assembly (1105) is counterbalanced and provides for Z axis travel.

FIG. 13B is a side view of multi-axis motion assembly (1120) shown in FIG. 13A. This view shows the upper horizontally oriented linear slide assembly (1103) which provides for X (or Y) axis travel at a position 90° from the linear slide assembly (1104). The arrangement of the slides (1103, 1104 and 1105) provides for multi-axis movement of a drive assembly mounted horizontally or vertically for different types of tests.

Figure 14C:
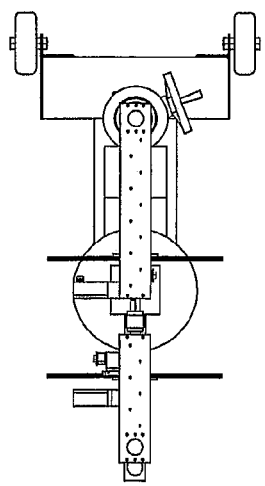
FIGS. 14A, 14B, and 14C are respective front, side, and top views of an embodiment of a self-contained test stand with dual drive (horizontal and vertical) assemblies that allows for quick change-over from bend testing to rotational testing, and vice versa, of the spinal specimen.
Figure 14A:
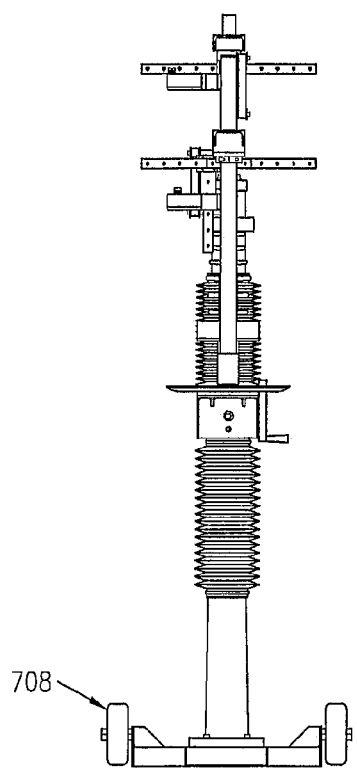
Figure 14B:
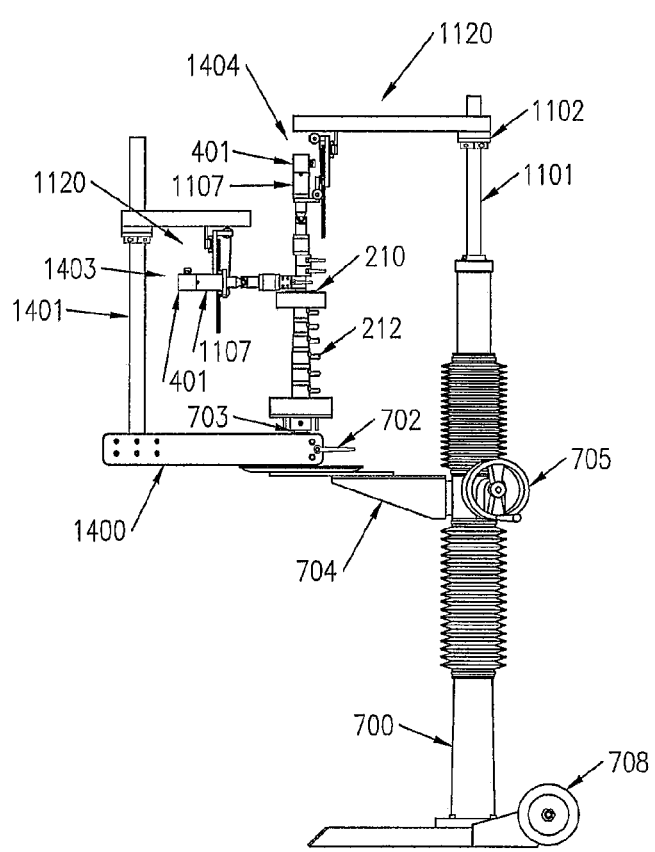

FIGS. 14A-14C are respective front, side, and top views of another embodiment drive mounting arrangement on a test stand (700). Advantages of this embodiment include: it is self-contained, highly adjustable to accommodate spinal specimens of many types and sizes, and portable for easy movement or relocation. Its open design allows for easy access to spinal specimen (212) and allows for clear views for use with medical imaging equipment. This is the same basic test stand (700) previously discussed in connection with FIGS. 7A-7C and 9A-9C but with two drive mounting arrangements (1403 and 1404) attached.

FIGS. 14A-14C show the ability to mount drive mounting arrangements (1403 and/or 1404) to the test stand (700). One drive mounting arrangement (1404) mounted in the vertical plane and the other drive mounting arrangement (1403) mounted in the horizontal plane may be attached to test stand (700) at the same time. One drive mounting arrangement (1403 or 1404) may be detached from specimen (212) and moved (rotated) out of the way. The purpose of having two drive mounting arrangements (1403 and 1404) on test stand (700) is to increase the speed that multiple tests may be performed with little time needed for change-over or set-up from test to test. It is envisioned that drive mounting arrangements (1403 and 1404) can be attached to spinal specimen (212) at the same time via a suitably designed clamp, like clamp (210), for simultaneous bending and torsion testing in two axes.

Figure 15B:
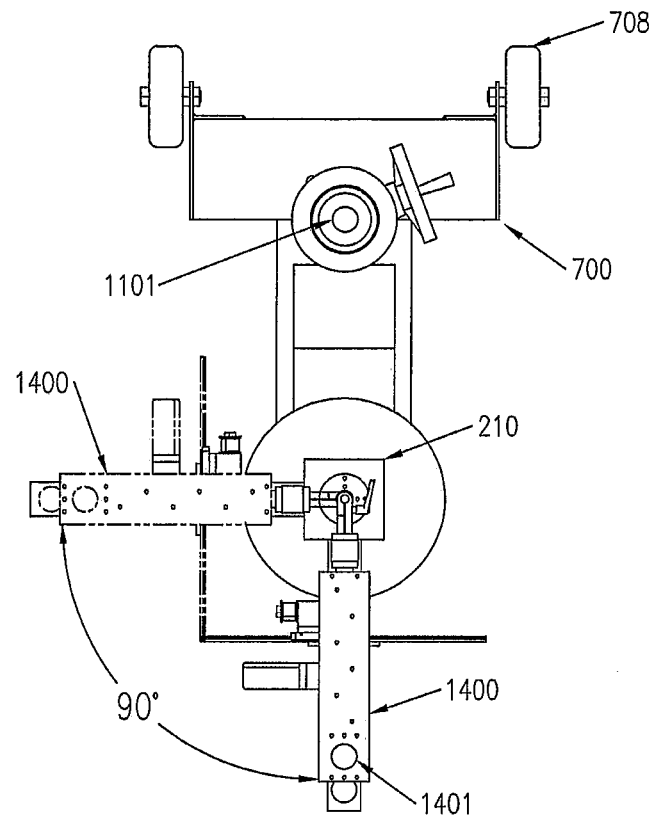

The side view of FIG. 14B best shows the associated parts. Test stand (700) can include wheels (708) for easy movement and table (704) which is movable up and down by use of hand wheel (705) employing a rack and pinion set and a clamp lock mechanism. Affixed to table (704) is a specimen mounting post (703) and attached to that post (703) is a horizontal arm (1400) which holds a vertical column (1401) at its distal end. This column (1401) supports horizontal drive mounting arrangement (1403) via an instance of multi-axis motion assembly (1120). A quick release clamp (702) at the end of arm (1400) nearest specimen mounting post (703) can be loosened to allow arm (1400) and, hence, the entire horizontal drive mounting arrangement (1403) to be rotated about the Z axis of specimen (212) when the specimen quick clamp (210) is also loosened. Rotation of horizontal drive mounting arrangement (1403) 90° will allow change over from extension-flexion testing to lateral bending testing, or vice versa, without repositioning spinal specimen (212). Arm (1400) can be locked at any angle along its arc of movement for specialized testing or just to move it out of the way when performing torsion tests about the Z axis of specimen (212). FIG. 15B is a top view of the test stand (700) in FIGS. 14A-14C showing a 90° rotation of arm (1400) for reference.

Figure 15A:
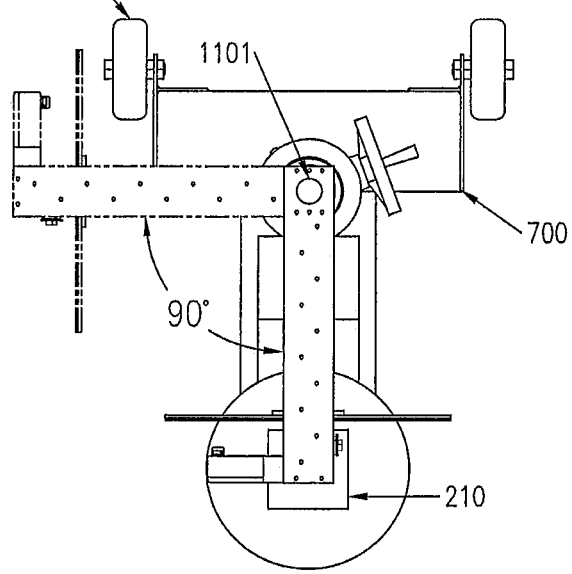

FIG. 14B also shows a second vertical column (1101) extending upward from test stand (700). This second column (1101) can be used to adjust the height of vertical drive mounting arrangement (1404) to accommodate various specimen sizes. Second column (1101) can be used to mount either a horizontal or vertical drive arrangement as shown in FIGS. 11A-11B or 12A-12B. FIG. 14B shows vertical drive mounting arrangement (1404) mounted to second column (1102) via another instance of multi-axis motion assembly (1120). FIG. 15A is a top view of test stand (700) in FIGS. 14A-14C showing vertical drive mounting arrangement (1404) rotating 90° (to the position shown in phantom) relative to spinal specimen (212) and then clamped in place when not in use.

Figure 16C:
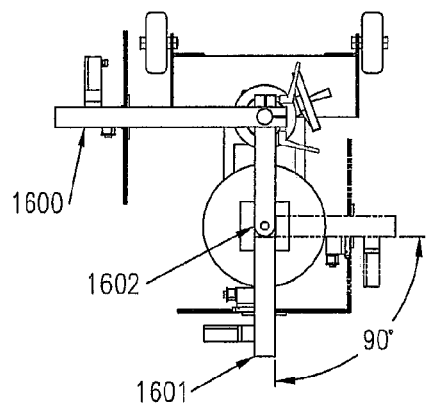
FIGS. 16A, 16B and 16C are respective front, side, and top views of an embodiment of a self-contained test stand with dual drive assemblies.
Figure 16A:
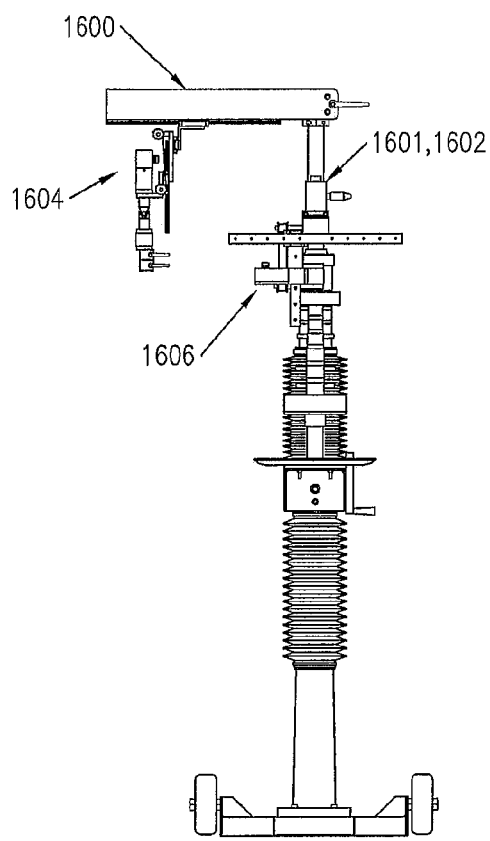
Figure 16B:
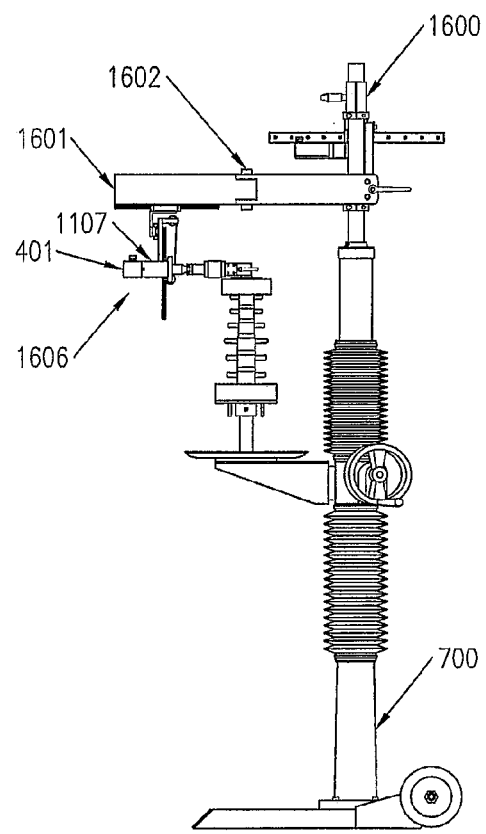

FIGS. 16A-16C show respective front, side and top views of another embodiment of drive mounting arrangements (1604 and 1606) mounted on portable test stand (700). The main difference between the embodiments shown in FIGS. 16A-16C and FIGS. 14A-14C is that drive mounting arrangements (1604 and 1606) are both mounted on arms (1600 and 1601) located above spinal specimen (212). This arm arrangement allows for an upper arm (1600) and attached drive mounting arrangement (1604) to be rotated out of the way (as shown in FIG. 16C) when bend testing is being performed. In addition, a lockable hinge (1602) on an arm (1601) allows the bend testing position to be repositioned from the front or rear to either side of spinal specimen (212) without moving the position of spinal specimen (212).

Figure 17C:
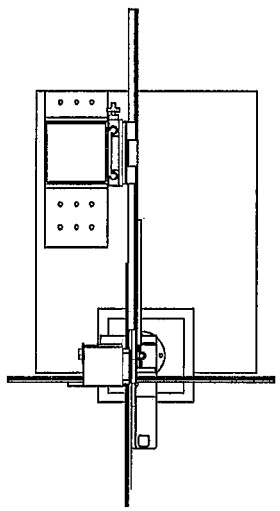
FIGS. 17A, 17B and 17C are respective front, side, and top views of an embodiment of a self-contained test stand with a single drive assembly positioned for rotational testing about the Z axis which can be mounted on a table or bench.
Figure 17A:
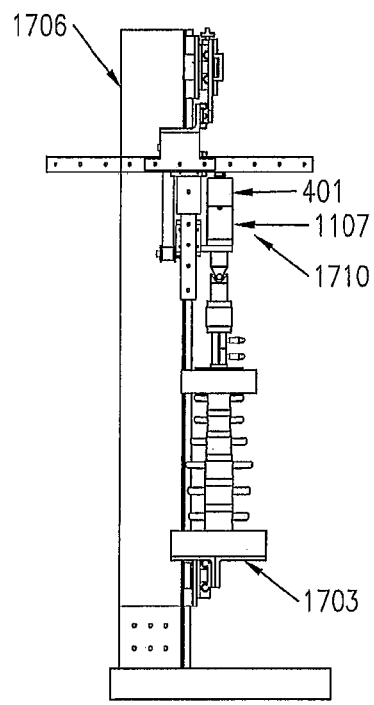
Figure 17B:
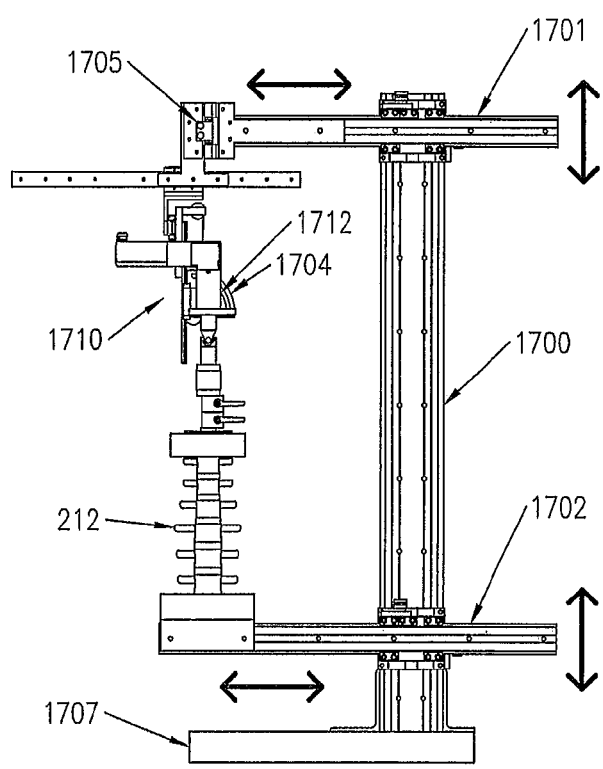
Figure 18C:
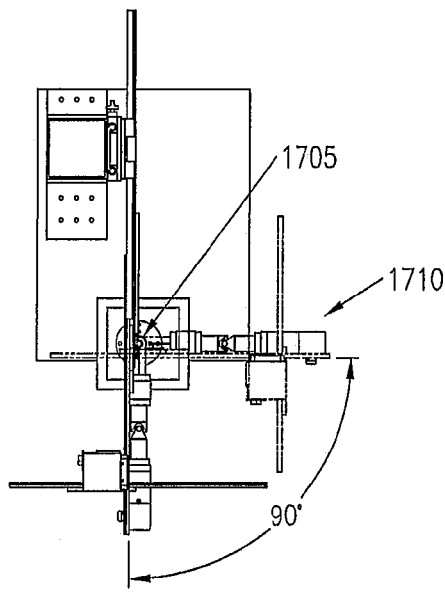
FIGS. 18A, 18B and 18C are respective side, front, and top views of the self-contained test stand of FIGS. 17A-17C with the drive assembly positioned for bend testing.
Figure 18A:
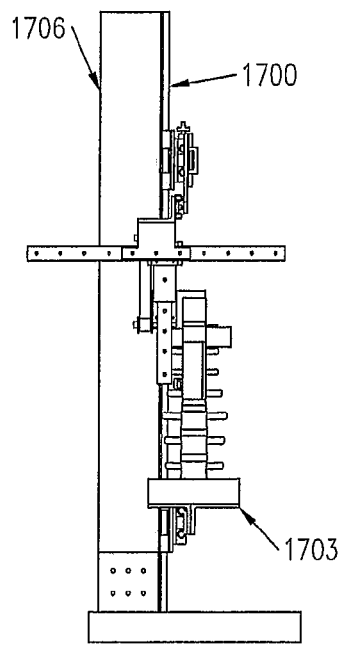
Figure 18B:
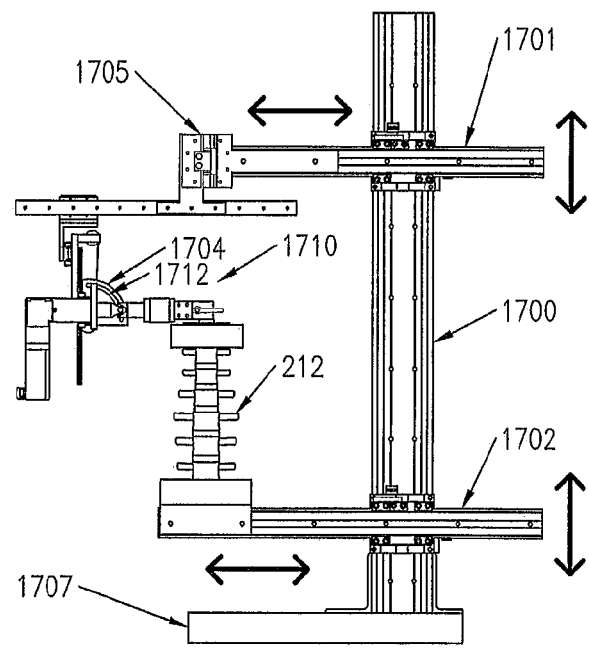

FIGS. 17A-17C and FIGS. 18A-18C show respective side, front and top views of a lightweight portable embodiment drive mounting arrangement (1710) which can be mounted on a table or bench. FIGS. 17A-17C show drive mounting arrangement (1710) in a vertical position for torsion testing of spinal specimen (212) about the Z axis thereof. FIGS. 18A-18C show the same drive mounting arrangement (1710) in a horizontal position for bend testing of spinal specimen (212). The embodiment shown in FIGS. 17A-18C includes two spaced, parallel horizontal slides (1701 and 1702) and one vertically adjustable slide (1700) that allows horizontal slides (1701 and 1702) to be repositioned in the horizontal plane and locked in place to position drive mounting arrangement (1710) and test specimen (212) quickly and easily. The single vertical slide (1700) is attached to a vertical post (1706) which is the backbone of the system, providing support for the other features and drive mounting arrangement (1710). This post (1706) is attached to a base (1707). The upper horizontal slide (1701) via vertical slide (1700) provides for up and down adjustment of drive mounting arrangement (1710). The lower horizontal slide (1702) provides for up and down adjustment of spinal specimen (212) and its mounting plate (1703). One concept shown in this version is that drive mount (1704) allows for repositioning of the drive mounting arrangement (1710) for horizontal X or Y axis testing (in FIGS. 18A-18C) or vertical Z axis testing (in FIGS. 17A-17C) of specimen (212) by way of a locking 90° slotted assembly (1712). In addition, upper horizontal slide (1701) has a locking hinge assembly (1705) located at its end nearest specimen (212) that allows drive mounting arrangement (1710) to swing 90° (as shown in FIG. 18C) to adjust the horizontal drive position for testing on either the X or Y axis of spinal specimen (212).

Figure 19:
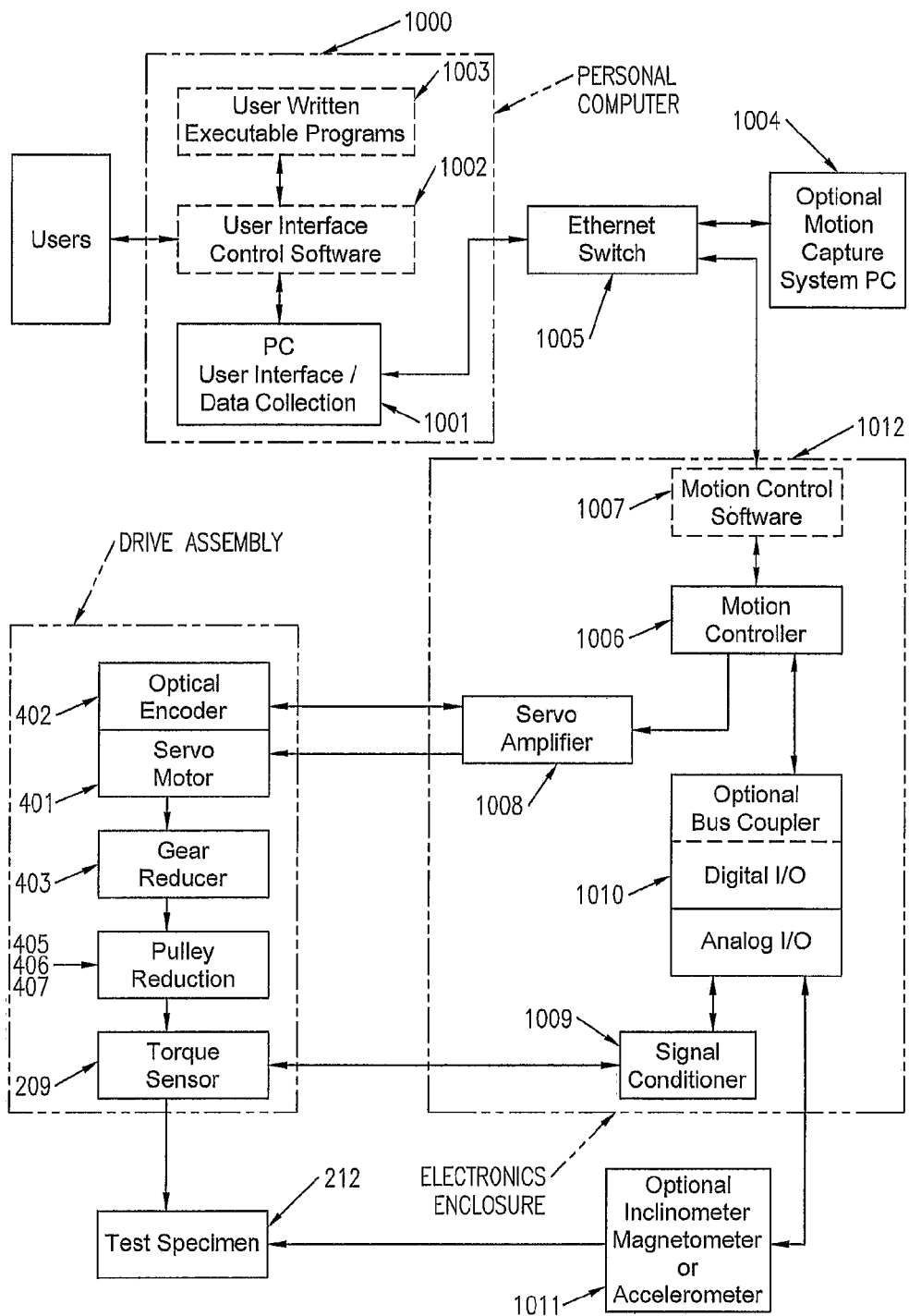
FIG. 19 is a block diagram of another control and data acquisition system that can be utilized in any embodiment of a sample testing device that includes dual drive assemblies that facilitate improved change-over when switching between bend and torsion testing.

FIG. 19 is a block diagram similar to the block diagram of FIG. 10. The difference between the two figures is that FIG. 19 illustrates an embodiment for controlling the operation of two drive assemblies without a physical change over or physical relocation of a drive assembly from one position to another. Each drive assembly in FIGS. 14A-14C and 16A-16C has its own gear reducer (1107), drive motor (401) and its own integral optical encoder (402) which is wired to its own servo amplifier (1008) in FIG. 19. Each drive assembly also includes its own torque sensor (209) which is attached to its own signal conditioner (1009) inside of enclosure (1012). This dual drive control embodiment allows faster, easier and safer change over between the differing test modes without having to physically change electrical and communication connections. It is not necessarily intended to allow the use of two drive systems concurrently.

Throughout this document different, non-limiting embodiments are disclosed. All disclosed embodiments desirably use sliding elements that provide low friction movement in multiple axes. All disclosed embodiments induce the test specimen to move by the application of torque at the specimen's top surfaces in the X, Y or Z axis of the specimen. All disclosed embodiments use a torque transducer to read and control applied force through closed loop feedback. All disclosed embodiments desirably use an optical encoder as a component of the drive system or a sensor attached directly to the specimen to provide accurate angular feedback and closed loop control. All disclosed embodiments lend themselves to easy mounting and use on a free-standing test stand, a table or a bench top.

The present invention has been described with reference to the accompanying figures. Obvious modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A sample testing device comprising:
   a motor;
   a gear reducer coupled to the motor;
   a spline adapter coupled to the motor via the gear reducer;
   the motor, the gear reducer and the spline adapter mounted to a body;
   a shaft supporting the body having the motor, the gear reducer and the spline adapter mounted thereto for linear motion on the shaft; and
   a ball spline shaft supported by the spline adapter substantially perpendicular to an axis of the shaft for rotation by the motor via the spline adapter and the gear reducer, wherein an end of the ball spline shaft opposite the spline adapter is coupleable to a sample under test.

2. The sample testing device of claim 1, wherein the body is adapted to move linearly on the shaft in response to rotation of the ball spline shaft via the motor and the gear reducer.

3. The sample testing device of claim 2, wherein the spline adapter and the ball spline shaft are adapted to enable translation of the ball spline shaft linearly along its axis during rotation of the ball spline shaft via the motor and the gear reducer.

4. The sample testing device of claim 1, wherein the spline adapter and the ball spline shaft are adapted to enable translation of the ball spline shaft linearly along its axis during rotation of the ball spline shaft via the motor and the gear reducer.

5. The sample testing device of claim 1, wherein the gear reducer includes: a planetary gear reducer, a pair of pulleys coupled by a belt, or both.

6. The sample testing device of claim 1, further including a pair of bearing blocks coupling opposite ends of the shaft for linear motion to a pair of linear shafts having axes disposed substantially perpendicular to the axis of the shaft.

7. The sample testing device of claim 6, wherein an axis of the ball spine shaft is disposed substantially parallel or substantially perpendicular with axes of the pair of linear shafts and substantially perpendicular to the axis of the shaft.

8. The sample testing device of claim 1, further including:
   a mounting arm; and
   a pair of columns coupled between the shaft and the mounting arm.

9. The sample testing device of claim 8, wherein the mounting arm is pivotally coupled to a table.

10. A sample testing device comprising:
    a motor;
    a gear reducer;
    an output shaft coupled for rotation by the motor via the gear reducer;
    a first device adapted to enable the output shaft to move linearly in a first direction substantially parallel with an axis of the output shaft; and
    a second device coupled to the first device for enabling the output shaft to move linearly in a second direction substantially perpendicular to the first direction.

11. The sample testing device of claim 10, further comprising a third device coupled to the first and second devices for enabling the output shaft to translate linearly in a third direction substantially perpendicular to the first and second directions.

12. The sample testing device of claim 10, wherein the first device is one of the following:
    a linear slide assembly; or
    a ball spline supporting the output shaft for linear translation thereof.

13. The sample testing device of claim 12, wherein the output shaft is a spline shaft.

14. The sample testing device of claim 10, wherein the second device is one of the following:
    a linear slide assembly; or
    a body supported by a shaft for linear motion thereon, wherein the motor, the gear reducer, and the output shaft are mounted to the body.

15. The sample testing device of claim 10, wherein the third device is one of the following:
    a linear slide assembly; or
    one or more shafts, each of which is coupled to the output shaft via a bearing block.

16. A sample testing device comprising:
    a multi-axis motion assembly;
    a motor supported by the multi-axis motion assembly;

a gear reducer supported by the multi-axis motion assembly; and an output shaft coupled for rotation by the motor via the gear reducer, wherein the multi-axis motion assembly is adapted to enable the combination of the motor, the gear reducer and the output shaft to move in substantially perpendicular directions, including a direction parallel with an axis of the output shaft, when the output shaft is rotatably driven by the motor via the gear reducer.

17. The sample testing device of claim 16, wherein the multi-axis motion assembly comprises a plurality of linear slide assemblies coupled together such that the plurality of linear slide assemblies are moveable in substantially perpendicular directions to each other.

18. The sample testing device of claim 16, wherein the multi-axis motion assembly is adapted to enable the combination of the motor, the gear reducer and the output shaft to move in three perpendicular directions.

19. The sample testing device of claim 16, further including a device for coupling the output shaft to a sample under test.

20. The sample testing device of claim 19, further including a device for repositioning the output shaft axis relative to the sample under test.

* * * * *